US007157082B2

(12) United States Patent
Backhaus

(10) Patent No.: US 7,157,082 B2
(45) Date of Patent: Jan. 2, 2007

(54) CARDIOPROTECTIVE THERAPIES BASED ON ENZYMATIC ELIMINATION OF LIPID PEROXIDES BY ALLENE OXIDE SYNTHASE

(75) Inventor: Ralph A. Backhaus, Phoenix, AZ (US)

(73) Assignee: Arizona Board of Regents, Tempe, AZ (US)

( * ) Notice: Subject to any disclaimer, the term of this patent is extended or adjusted under 35 U.S.C. 154(b) by 95 days.

(21) Appl. No.: 10/630,548

(22) Filed: Jul. 30, 2003

(65) Prior Publication Data

US 2004/0213775 A1    Oct. 28, 2004

(51) Int. Cl.
    A01N 61/00    (2006.01)
(52) U.S. Cl. .................... 424/94.1; 435/232; 435/233
(58) Field of Classification Search ............... 435/233, 435/232; 424/94.1
    See application file for complete search history.

(56) References Cited

U.S. PATENT DOCUMENTS 6,132,711 A * 10/2000 Backhaus et al. .......... 424/94.1

OTHER PUBLICATIONS

Abunasra, et al., (2001), European Journal of Cardio-thoracic Surgery, "Efficacy of adenoviral gene transfer with manganese superoxide dismutase and endothelial nitric oxide synthase in reducing ischemia and reperfusion injury", vol. 20, pp. 153-158.
Backhaus, et al., (1997), FASEB Journal, "Dual Roles of Allene Oxide Synthase, The Abundant Cytochrome P450 of Guayule Rubber Particles", (P35), p. A776.
Brown, et al., (2005), JAMA, "Is There Any Hope for Vitamin E", vol. 293(11), pp. 1387-1390.
Cuzzocrea, et al., (2001), "Antioxidant therapy: A new pharmacological approach in shock, inflammation, and ischemia/reperfusion injury", Pharmacol Rev., vol. 53(1), pp. 135-159.
Delanty, et al., (2000), Arch Neurol, "Antioxidant Therapy in Neurologic Disease", vol. 57, pp. 1265-1270.
Dhalla, et al., (2000), Cardiovascular Research, "Status of myhocardial antioxidants in ischemia-reperfusion injury", vol. 47, pp. 446-456.
Flaherty, et al., (1994), Circulation, "recombinant Human Superoxide Dismutase (h-SOD) Fails to Improve Recovery of Ventricular Function in Patients Undergoing Coronary Angioplasty for Acute Myocardial Infarction", vol. 89(5), pp. 1982-1991.
Galang, et al., (2000), Toxicology, "Apoptotic cell death during ischemia/reperfusion and its attenuation by antioxidant therapy", vol. 148, pp. 111-118.
Gladstone, et al., (2002), Stroke, "Toward Wisdom from Failure: Lessons from Neuroprotective Stroke Trials and New Therapeutic Directions", Comments, Opinion, and Reviews, vol. 33, pp. 2123-2136.
Hangaishi, et al., (2001), Biochemical and Biophysical Research Communications, "Lecithinized Cu, Zn-Superoxide Dismutase Limits the Infarct Size Following Ischemia-Reperfusion Injury in Rat Hearts in Vivo", vol. 285, pp. 1220-1225.
Huynh, et al., (1999), Journal of Surgical Research, "Reduction of Lipid Peroxidation with Intraoperative Superoxide Dismutase Treatment Decreases Intimal Hyperplasia in Experimental Vein Grafts", vol. 84, pp. 223-232.
Kanamasa, et al., (2001), Acta Cardiol, "Protective effect of PEG-SOD against early coronary reperfusion injury assessed in reperfused and non-reperfused ischaemic areas of the same heart", vol. 56, pp. 181-186.
Keith, et al., (2001), Am. J. Clin. Nutr., "A Controlled Clinical Trial of Vitamin E Supplementation in Patients with Congestive Heart Failure", vol. 73, pp. 219-224.
Kesavulu, et al., (2001), Diabetes Research and Clinical Practice, "Lipid Peroxidation and antioxidant enzyme status in Type 2 Diabetics with Coronary heart disease", vol. 53, pp. 33-39.
Kilgore, et al., (1993), Clin Biochem, "Reperfusion Injury After Myocardial Infarction: The Role of Free Radicals and the Inflammatory Response", vol. 26, pp. 359-370.
Kloner, et al., (1993), JACC, "Does ReperfusionInjury Exist in Humans", vol. 21(2), pp. 537-545.
Laurindo, et al., (1991), Circulation, "Evidence for superoxide radical-dependent coronary vasospasm after angioplasty in intact dogs", vol. 83, pp. 1705-1715.
Li Q, et al., (2001), "Gene therapy with extracellular superoxide dismutase protects conscious rabbits against myocardial infarction" Circulation, vol. 103(14), pp. 1893-1898.
Miki, et al., (1999), Basic Res. Cardiol, "Failure of N-2-mercaptopropionyl glycine to reduce myocardial infarction after 3 days of reperfusion in rabbits", vol. 94, pp. 180-187.
Pan Z, et al., (1998), "Aspirin inhibition and acetylation of the plant cytochrome P450, allene oxide synthase, resembles that of animal prostaglandin endoperoxide H synthase", J. Biol. Chem., vol. 273(29), pp. 18139-18145.
Prasad, et al., (1996), Can J. Cardiol, "Superoxide dismutase and catalase in protection of cardiopulmonary bypass-induced cardiac dysfunction and cellular injury", vol. 12(10), pp. 1083-1091.
Rowland, et al., (1995), Surgury, "Mechanisms of immature myocardial tolerance to ischemia: Phenotypic differences in antioxidants, stress proteins, and oxidases", vol. 118(2), pp. 446-452.

(Continued)

Primary Examiner—Leon Blaine Lankford, Jr.
(74) Attorney, Agent, or Firm—McDonnell Boehnen Hulbert & Berghoff LLP

(57) ABSTRACT

The present invention relates to methods and compositions related to the use of enzymes of the allene oxide synthase family for reducing myocardial ischemia reperfusion injury associated with myocardial infarction, thrombolysis, angioplasty and coronary bypass surgery. The methods of the invention comprise administration of allene oxide synthases, which are capable of eliminating lipid hydroperoxides, as a potent cardioprotective agent. The invention is based on the discovery that administration of allene oxide synthase following severe global ischemia stimulates cardiac recovery.

19 Claims, No Drawings

OTHER PUBLICATIONS

Shutenko, et al., (1999), Biochemical Pharmacology, "Influence of the Antioxidant Quercetin In Vivo on the Level of Nitric Oxide Determined by Electron Paramagnetic Resonance in Rat Brain during Global Ischemia and Reperfusion", vol. 57, pp. 199-208.

Stranges, et al., (2006), Am. J. Epidemiol, "Effects of Selenium Supplementation on Cardiovascular Disease Incidence and Mortality: Secondary Analyses in a Randomized Clinical Trial", vol. 163(8), pp. 694-699.

Tirilazad International Steering Committee, (2000), Stroke, "Tirilazad Mesylate in Acute Ischemic Stroke, A Systematic Review, Comments, Opinions, and Reviews", pp. 2257-2265.

Van Remmen, et al., (2001), "Knockout mice heterozygous for Sod2 show alterations in cardiac mitochondrial function and apoptosis", Am J. Physiol. Heart Circ. Physiol., vol. 281(3), pp. H1422-H1432.

Venturini, et al., (1998), Journal of Thrombosis and Thrombolysis, "The Antioxiidant, N-(2-mercaptopropionyl)-glycine (MPG), Does Not Reduce Myocardial Infarct Size in an Acute Canine Model of Myocardial Ischemia and Reperfusion", vol. 5, pp. 135-141.

Wall, (2000), Pharmacology "Antioxidants in Prevention of Reperfusion Damage of Vascular Endothelium", vol. 1, pp. 67-71.

The HOPE and HOPE-TOO Trial Investigators, Eva Lonn, et al., (2005), JAMA, "Effects of Long-Term Vitamin E Supplementation on Cardiovascular Events and Cancer", vol. 293(11), pp. 1338-1347.

Zhiqiang, et al., (1996), Plant Physiology, American Society of Plant Physiologists, "Heterologous Expression and Analysis of Allene Oxide Synthase, The Rubber-Associated P450 From Guayule", (2 Suppl), pp. 98-eoa.

\* cited by examiner

CARDIOPROTECTIVE THERAPIES BASED ON ENZYMATIC ELIMINATION OF LIPID PEROXIDES BY ALLENE OXIDE SYNTHASE

SPECIFICATION

The present invention relates to methods and compositions related to the use of enzymes of the allene oxide synthase family for reducing myocardial ischemia reperfusion injury associated with myocardial infarction, thrombolysis, angioplasty and coronary bypass surgery. The methods of the invention comprise administration of allene oxide synthases, which are capable of eliminating lipid hydroperoxides, as a potent cardioprotective agent. The invention is based on the discovery that administration of allene oxide synthase following severe global ischemia stimulates cardiac recovery.

BACKGROUND OF INVENTION

Ischemia, the clinical term for oxygen starvation, is the leading cause of death in the world. The most common forms of ischemia leading to death are caused by interruptions of blood flow. Heart disease, stroke, and severe blood loss from traumatic injuries are examples of ischemia that are responsible for over 50% of all deaths.

In clinical situations of ischemia, the immediate goal is to restore blood flow to the patient as quickly as possible. If blood flow is restored within a suitable time period, tissue damage can be averted. However, a significant delay in restoring blood flow leads to a second condition known as ischemia-reperfusion injury. Reperfusion injury begins when harmful reactive oxygen species are formed following the ischemic episode. Reactive oxygen species originate by complex, spontaneous free radical reactions that damage lipids, proteins and DNA and can eventually kill cells. Lipids in cellular membranes are the primary early targets of attack by oxygen in the blood resulting in formation of lipid peroxides which are extremely cytotoxic (Kilgore K S and Lucchesi B R. 1993, Clin Biochem 26:359–70; Kloner R A., 1993, J Am Coll Cardiol 21:537–45; Huynh T T, et al., 1999, J Surg Res 84:223–32; Kesavulu M M, et al., 2001, Diabetes Res Clin Pract 53:33–9).

Ischemia-reperfusion injury can develop gradually after an ischemic event and may cause irreversible damage to tissues. Clinical examples include cardiac contractile dysfunction, arrhythmias and irreversible myocyte damage (heart cell death) following myocardial infarction (heart attack). Although no drugs are currently available for treating ischemia-reperfusion injury, the damage caused by ischemia-reperfusion injury is preventable and reversible if certain treatments are administered in a timely fashion. The most clinically relevant treatments involve administration of antioxidants. Endogenous antioxidants such as glutathione peroxidase (GPX), superoxide dismutase (SOD), and catalase act as a primary defense mechanism. Additionally, dietary vitamin E can play a secondary role in attenuating ischemia-reperfusion injury. Administration of exogenous antioxidant supplements before or after reperfusion has shown some utility in experimental systems (Abunasra H J et al., 2001, Eur J Cardiothorac Surg. 20: 153–8; Cuzzocrea S, et al., 2001, Pharmacol Rev Mar 53:135–59; Dhalla N S, et al., 2000, Cardiovasc Res 47:446–56; Galang N, et al, 2000, Toxicology 148:111–8; Hangaishi M, et al., 2001, Biochem Biophys Res Commun 285:1220–5; Kanamasa K, et al., 2001, Acta Cardiol 56: 181–6; Laurindo F R, et al., 1991, Circulation 83:1705–15; Li Q, 2001, Circulation 103: 1893–8; Prasad K, et al., 1996, Can J Cardiol 12:1083–91; Rowland R T, et al.,1995, Surgery 118:446–52; Van Remmen H, et al., 2001, Am J Physiol Heart Circ Physiol 281 :H1422–32). However, SOD treatment has failed to show a beneficial effect in human clinical trials (Flaherty J T, 1994, Circulation 89: 1982–91).

Allene Oxide synthase serves as an antioxidant by rapidly eliminating lipid hydroperoxides from the system (U.S. Pat. No. 6,132,711; Pan Z, et al., 1998, J Biol Chem 273: 18139–18145). The present invention provides a novel method for reducing ischemia-reperfusion injury based on the administration of allene oxide synthase.

SUMMARY OF THE INVENTION

The present invention relates to methods and compositions related to the use of enzymes of the family of allene oxide synthetases for reducing myocardial ischemia reperfusion injury associated with myocardial infarction, thrombolysis, angioplasty and coronary bypass surgery. The methods of the invention comprise administration of allene oxide synthases as a potent cardioprotective agent against ischemia reperfusion injury. The invention is based on the discovery that administration of allene oxide synthase following severe global ischemia is capable of stimulating cardiac recovery.

DETAILED DESCRIPTION OF THE INVENTION

The present invention provides for compositions comprising enzymes of the allene oxide synthase family and the use of such compositions for prevention and/or treatment of cardiovascular disease. Such cardiovascular diseases include, for example, myocardial infarction, angina pectoris, thrombolysis, angioplasty, coronary bypass surgery, vascular or myocardial ischemia, and related conditions as would be known by those of skill in the art which involve dysfunction of, or damage to, the heart or vasculature, and in particular, to tissue damage related to accumulation of cytotoxic lipid hydroperoxides.

In addition, the compositions and methods of the present invention may be used to treat other types of ischemias relating to accumulation of cytotoxic hydroperoxides in affected tissues. Such ischemias include but are not limited to mesenteric, brain (stroke), limb, optical and hepatic ischemias.

Many allene oxide synthases are known and, thus, can be produced by known methods from known starting materials, or may be prepared by methods used to prepare allene oxide synthases as described in the literature. For example, allene oxide synthase may be recombinantly expressed as described in U.S. Pat. No. 6,132,711. Alternatively, the allene oxide synthase may be commercially obtained. For purposes of the present invention, any member of the allene oxide synthase family may be utilized provided that the selected enzyme is capable of reducing the level of cytotoxic lipid hydroperoxides.

The present invention provides pharmaceutical compositions comprising an allene oxide synthase in a pharmaceutically acceptable carrier. Such carriers include any suitable physiological solution or dispersant or the like, such as saline or buffered saline. Carriers may also include, for example, any diluent, excipient, suspending agent, lubricating agent, adjuvant, vehicle, delivery system, emulsifier, absorbent, perservative, surfactant, colorant, flavorant or sweetener, antibacterial and antifungal agents, isotonic and adsorption delaying agents, and the like. Except insofar as any conventional media, carrier or agent is incompatible with the active ingredient, its use in the compositions is contemplated.

The present invention is further directed to methods for prevention and/or treatment of cardiovascular disease. The invention finds particular utility in connection with surgical procedures such as coronary bypass. In such instances, the allene oxide synthase would normally be administered prior to, and if necessary, following the procedure. The allene oxide synthase may also be used prior to or during ischemia reperfusion after a spontaneous ischemic event. Such spontaneous events include but are not limited to subjects having coronary occlusion.

The method of the invention comprises the steps of administering into a subject prior to and/or at the time of ischemia reperfusion injury an amount of allene oxide synthase capable of reducing the level of lipid hydroperoxides and allowing the allene oxide synthase to come into effective contact with the tissue for reducing the ischemia reperfusion injury. The compositions of the invention may be administered using a variety of different methods, including but not limited to oral, pulmonary, parenteral (intramuscular, intraarticular, intraperitoneal, intravenous (IV) or subcutaneous injection), inhalation (via a fine powder formulation or a fine mist), transdermal, nasal, vaginal, rectal, or sublingual routes of administration and can be formulated in dosage forms appropriate for each route of administration.

In preferred embodiments of the invention, the allene oxide synthase is administered prior to ischemia reperfusion injury, typically by infusion of allene oxide synthase into the bloodstream. Alternatively, the allene oxide synthase is administered during ischemia reperfusion injury and prior to termination of tissue damage resulting from ischemia reperfusion injury. In instances, where the allene oxide synthase is administered following commencement of ischemia reperfusion injury, administration should be done within five days of such commencement, more preferably within twenty-four hours after commencement, and most preferably within one hour after commencement of injury.

Dosage of the compositions of the present invention to be administered is determined with reference to various parameters, including the species of the subject, the age, weight, and disease status and the particular physiological conditions requiring phenotypic alteration. The dosage is preferably chosen so that administration causes an effective result, as measured by molecular assays or phenotypic alteration. Such assays include, for example, measurement of cardiac function, i.e., systolic and diastolic pressure, contractibility and cardiac output.

6. EXAMPLE

Allene Oxide Syhthase Stimulates Recovery of Mechanical Function of Hearts Following Ischemia

6.1. Material and Methods

Animals

Male Wistar rats (300–350 g) were obtained from Charles River Laboratories. Animals were housed two per cage and had free access to food (standard rat chow) and water. Animals used in this study were cared for according the recommendations in The guide for the Care and Use of Laboratory Animals, National Institute of Health, Publ. No. 85-23, revised 1986.

Ischemic Protocol

Hearts from previously $CO_2$-gassed and decapitated rats were perfused and cannulated as Working hearts. Briefly, hearts were quickly excised, placed in ice-cold buffer, and immediately perfused retrogradely via the aorta with Krebs-Henseleit buffer containing in (mM): 118 NaCl, 4.7 KCl, 1.2 $KH_2PO_4$, 1.2 $MgSO_4$, 2.5 $CaCl_2$, 0.5 EDTA, 25 $NaHCO_3$, 11 glucose, 1.75 $Ca^{2+}$ (pH 7.4, gassed with 95% $O_2$–5% $CO_2$). During this perfusion, the hearts were trimmed of excess tissue and the openings of the left atria were cannulated. Hearts were then switched to the working mode and perfused at a 11.5 mmHg left atrial filling pressure and 80 mmHg aortic afterload in a recirculating buffer system containing 11 mM glucose and 1.2 mM palmitate prebound to 3% bovine serum albumin. Hearts were perfused with this concentration of fatty acid since it mimics that observed in the clinical setting of ischemia and reperfusion associated with cardiac surgery. After 15 minutes of aerobic perfusion, hearts were subjected to 30 minutes of global ischemia by clamping off both left atrial filling and aortic afterload line. Following ischemia, left atrial and aortic flow were restored and hearts reperfused for 30 minutes. Allene oxide synthase, when used, was added directly into the perfusate at the concentration of 250 µg 15 minutes prior to the reperfusion period. At the end of reperfusion, hearts were removed from the cannulae and frozen in liquid $N_2$. Heart function was recorded using Transonic in-line flow probes (model T206) and a Dig Med Heart Performance Analyzer (model HPA-tau). Throughout the entire perfusion protocol, water jacketed chambers kept the temperature of the perfusate at 37° C.

Statistical Analysis

For statistical comparison of group means, the Student t-lest was used. A value of $p<0.05$ was considered significant. All data are reported as mean±SEM.

6.2. Results

Table 1 shows the effects of ADS on reperfusion recovery of hearts following severe global ischemia. Under aerobic conditions, mechanical function was similar between hearts from control and allene oxide synthase-treated groups. However, following 30 minutes of severe no-flow ischemia, allene oxide synthase was of benefit on recovery of mechanical function. In fact, as early as 5 minutes into reperfusion, recovery of systolic pressure, end-diastolic pressure, contractility, and CO in allene oxide synthase-treated was significantly improved compared to non-treated hearts. Throughout the remaining of the reperfusion period, the benificial effects of allene oxide synthase on systolic pressure, contractility, and cardiac output were observed.

A burst of oxygen free radicals typically observed upon reperfusion of ischemic hearts exposed to high levels of palmitate can result in cardiac dysfunction. It is clear that allene oxide synthase added prior to the onset of reperfusion is of benefit.

TABLE 1

Effects of AOS on reperfusion recovery following ischemia.

| Group | HR (beats/min) | PSP (mmHg) | EDP (mmHg) | +dP/dt (mmHg/sec) | −dP/dt (mmHg/sec) | CO (ml/min) |
| --- | --- | --- | --- | --- | --- | --- |
| Aerobic perfusion control | 231 ± 11 | 104 ± 3 | 47 ± 2 | 1898 ± 160 | 1243 ± 100 | 41 ± 5 |
| +AOS | 223 ± 6 | 116 ± 4 | 44 ± 2 | 2089 ± 124 | 1372 ± 152 | 46 ± 2 |
| 5 min reperfusion control | 174 ± 24 | 56 ± 18 | 33 ± 5 | 743 ± 429 | 455 ± 193 | 12 ± 9 |
| +AOS | 221 ± 11 | 112 ± 3† | 48 ± 1† | 2152 ± 157† | 1232 ± 159† | 40 ± 2† |
| 10 min reperfusion control | 164 ± 3 | 75 ± 12 | 41 ± 2 | 795 ± 494 | 831 ± 108 | 10 ± 5 |
| +AOS | 210 ± 16 | 117 ± 7† | 42 ± 4 | 2149 ± 119† | 1340 ± 177† | 42 ± 4‡ |
| 20 min reperfusion control | 172 ± 19 | 82 ± 11 | 44 ± 3 | 1093 ± 359 | 831 ± 132 | 17 ± 9 |
| +AOS | 221 ± 7 | 119 ± 4† | 43 ± 1 | 2472 ± 101‡ | 1482 ± 140† | 50 ± 4† |
| 30 min reperfusion control | 190 ± 18 | 85 ± 8 | 50 ± 3 | 1174 ± 241 | 727 ± 169 | 16 ± 9 |
| +AOS | 234 ± 4† | 118 ± 4‡ | 42 ± 1 | 2603 ± 155‡ | 1650 ± 124‡ | 56 ± 3‡ |

Values are reported as mean ± SEM for 4 animals for each group. HR, heart rate; PSP, peak systolic pressure; EDP, end diastolic pressure; +dP/dt, rate of contraction; −dP/dt, rate of relaxation; CO, cardiac output.
†significant compared to the control group, $p < 0.05$.
‡significant compared to the control group, $p < 0.01$.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims. Various references are cited herein, the disclosure of which are incorporated by reference in their entireties.

What is claimed is:

1. A method of treating ischemic injury comprising administering to a subject at a site of ischemic injury allene oxide synthase protein in an amount effective to treat the ischemic injury.

2. The method of claim 1, wherein said ischemic injury is myocardial infarction.

3. The method of claim 1, wherein said ischemic injury is cerebrovascular stroke.

4. A method of reducing ischemia-reperfusion injury comprising administering to a subject in need thereof allene oxide synthase protein in an amount effective to reduce ischemia-reperfusion injury, wherein the subject suffers from one or more condition selected from the group consisting of coronary artery occlusion, myocardial infarction, angina pectoris, thrombolysis, myocardial ischemia, mesenteric ischemia, cerebrovascular stroke, hepatic ischemia, limb ischemia, and optical ischemia; and/or the subject is undergoing or has undergone a procedure selected from the group consisting of angioplasty and coronary artery bypass surgery.

5. The method of claim 4, wherein the subject suffers from myocardial infarction.

6. The method of claim 4, wherein the subject suffers from cerebrovascular stroke.

7. The method of claim 4, wherein the subject is undergoing or has undergone a procedure selected from the group consisting of angioplasty and coronary bypass surgery.

8. The method of claim 1 wherein the ischemic injury is angina pectoris.

9. The method of claim 4 wherein the subject suffers from angina pectoris.

10. The method of claim 1 wherein the isehemic injury is thrombosis.

11. The method of claim 4 wherein the subject suffers from thrombolysis.

12. The method of claim 4 wherein the subject suffers from coronary artery occlusion.

13. The method of claim 4 wherein the subject suffers from myocardial ischemia.

14. The method of claim 4 wherein the subject suffers from mesenteric ischemia.

15. The method of claim 4 wherein the subject suffers from hepatic ischemia.

16. The method of claim 4 wherein the subject suffers from optical ischemia.

17. The method of claim 4 wherein the subject suffers from limb ischemia.

18. The method of claim 4, wherein the subject is undergoing or has undergone an angioplasty procedure.

19. The method of claim 4, wherein the subject is undergoing or has undergone coronary bypass surgery.

* * * * *